(12) United States Patent
Damle et al.

(10) Patent No.: US 9,814,585 B2
(45) Date of Patent: Nov. 14, 2017

(54) IMPLANT SET HAVING MODULARITY WITH CONFORMITY FOR TOTAL KNEE REPLACEMENT

(71) Applicants: Narendra Damle, Maharashtra (IN); Ravindra Vartak, Maharashtra (IN)

(72) Inventors: Narendra Damle, Maharashtra (IN); Ravindra Vartak, Maharashtra (IN)

( * ) Notice: Subject to any disclaimer, the term of this patent is extended or adjusted under 35 U.S.C. 154(b) by 0 days.

(21) Appl. No.: 15/043,204

(22) Filed: Feb. 12, 2016

(65) Prior Publication Data

US 2016/0228254 A1 Aug. 11, 2016

Related U.S. Application Data

(63) Continuation of application No. PCT/IN2014/000370, filed on Jun. 2, 2014.

(30) Foreign Application Priority Data

Jun. 1, 2013 (IN) .......................... 623/MUM/2013

(51) Int. Cl.
*A61F 2/38* (2006.01)
*A61F 2/30* (2006.01)

(52) U.S. Cl.
CPC .............. *A61F 2/3859* (2013.01); *A61F 2/38* (2013.01); *A61F 2/389* (2013.01); *A61F 2/3877* (2013.01); *A61F 2002/30616* (2013.01); *A61F 2250/0064* (2013.01)

(58) Field of Classification Search
CPC ........ A61F 2/38; A61F 2/3859; A61F 2/3877; A61F 2/389

USPC ..................... 623/20.27, 20.28, 20.14, 20.15
See application file for complete search history.

(56) References Cited

U.S. PATENT DOCUMENTS

| 5,597,384 | A | 1/1997 | Walker et al. |
| 7,628,818 | B2 * | 12/2009 | Hazebrouck ............ A61F 2/389 623/20.14 |
| 8,337,564 | B2 * | 12/2012 | Shah ......................... A61F 2/38 623/20.15 |

(Continued)

FOREIGN PATENT DOCUMENTS

| EP | 2 574 311 | 4/2013 |
| WO | WO 2012/018567 | 2/2012 |

OTHER PUBLICATIONS

International Preliminary Report on Patentability dated Dec. 1, 2015 issued in corresponding application No. PCT/IN2014/000370.

(Continued)

*Primary Examiner* — Alvin Stewart
(74) *Attorney, Agent, or Firm* — Cozen O'Connor

(57) ABSTRACT

An implant set having modularity with conformity for total knee replacement. The set having a femoral metal component, Tibial Component (4) with locked tibial Insert (2) therein and Patella to provide the exact conformity of combination of femoral component (1) and tibial component (4). The improvement involves such way that each of the Femoral component (1) to tibial insert (2) pair, there will be at least three sizes of tibial components (4) available, namely, a minus size tibial component (4), a standard tibial component (4), and a plus size tibial component (4); the dimensions of the locking mechanism will be same on all the three sizes, i.e. on minus size, standard size, and plus size.

12 Claims, 6 Drawing Sheets

TIBIAL COMPONENT
MINUS DIMENSION

TIBIAL COMPONENT
PLUS DIMENSION

(56) References Cited

U.S. PATENT DOCUMENTS

| | | | | |
|---|---|---|---|---|
| 8,562,687 B2* | 10/2013 | Faccioli | | A61F 2/38 623/20.14 |
| 2007/0203582 A1 | 8/2007 | Campbell | | |
| 2008/0091272 A1 | 4/2008 | Aram | | |
| 2008/0167722 A1* | 7/2008 | Metzger | | A61F 2/30721 623/20.36 |
| 2011/0251695 A1* | 10/2011 | Lenz | | A61F 2/0811 623/20.15 |
| 2012/0022658 A1* | 1/2012 | Wentorf | | A61F 2/389 623/20.28 |
| 2012/0022660 A1* | 1/2012 | Wentorf | | A61F 2/389 623/20.32 |
| 2012/0136452 A1* | 5/2012 | Richter | | A61F 2/3886 623/20.28 |
| 2012/0203350 A1* | 8/2012 | Hagen | | A61F 2/38 623/20.22 |
| 2013/0006372 A1* | 1/2013 | Wyss | | A61F 2/3886 623/20.27 |
| 2013/0024001 A1* | 1/2013 | Wentorf | | A61F 2/389 623/20.32 |
| 2013/0079885 A1* | 3/2013 | Meier | | A61F 2/38 623/20.21 |
| 2013/0184829 A1* | 7/2013 | Wyss | | A61F 2/38 623/20.28 |
| 2013/0184830 A1* | 7/2013 | Hazebrouck | | A61F 2/38 623/20.29 |
| 2016/0184107 A1* | 6/2016 | Parisi | | A61F 2/3886 623/20.15 |
| 2016/0228254 A1* | 8/2016 | Damle | | A61F 2/38 |

OTHER PUBLICATIONS

Writtten Opinion dated Nov. 12, 2014 issued in corresponding application No. PCT/IN2014/000370.

* cited by examiner

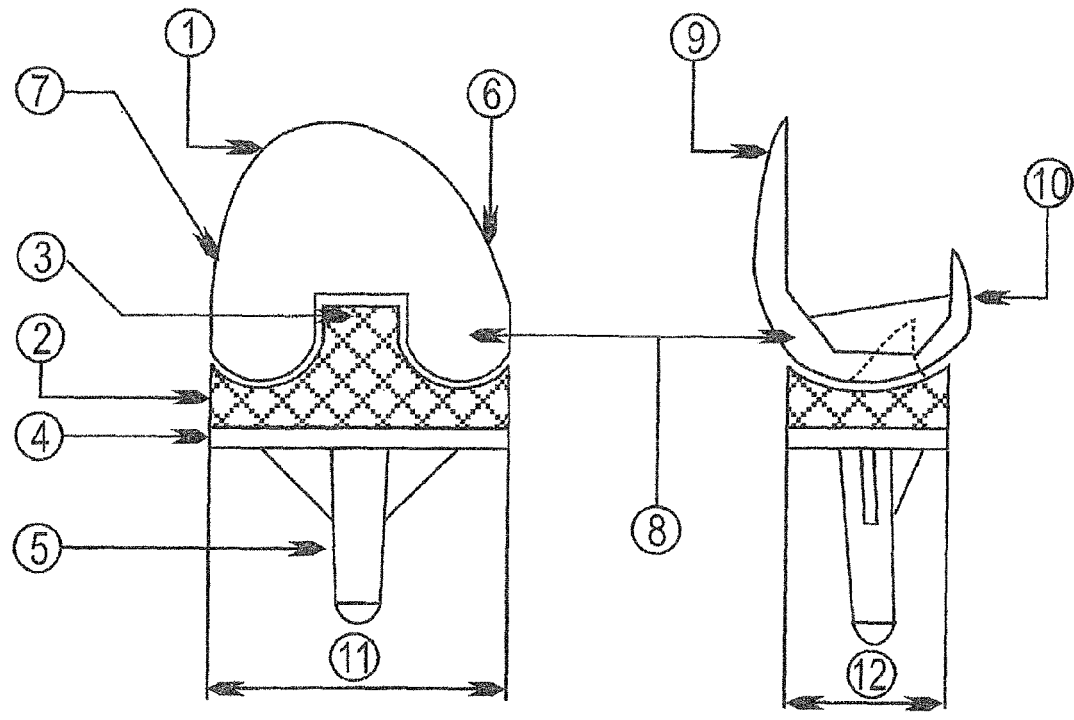
Fig : 1A    Fig : 1B
MODULAR TOTAL KNEE REPLACEMENT IMPLANT ASSEMBLY
POSTERUIR CRUCIATE LIGAMENT SUBSTITUTING
& FIXED BEARING DESIGN

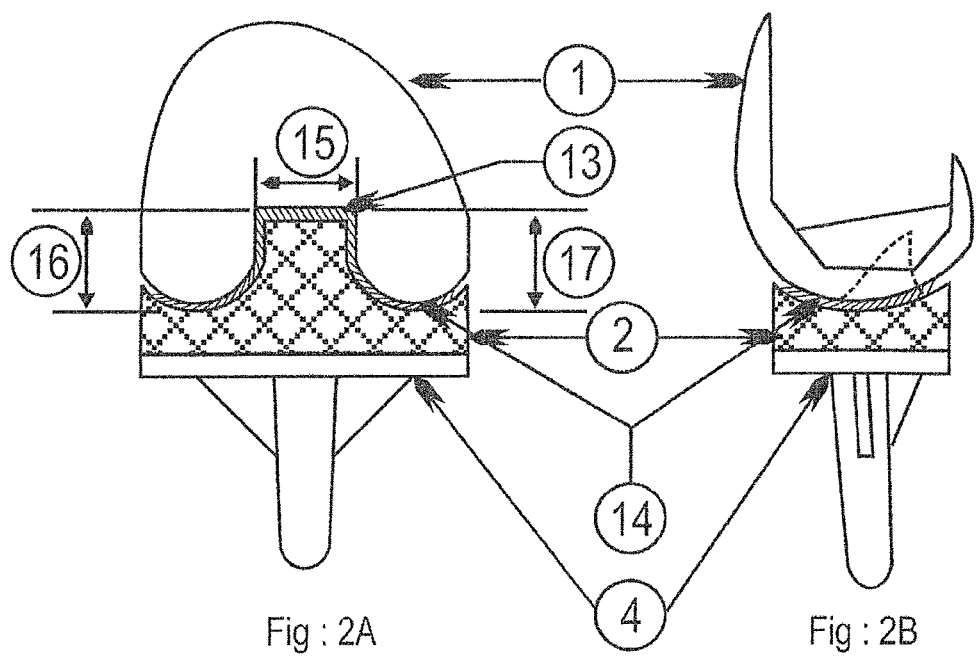
Fig : 2A   Fig : 2B

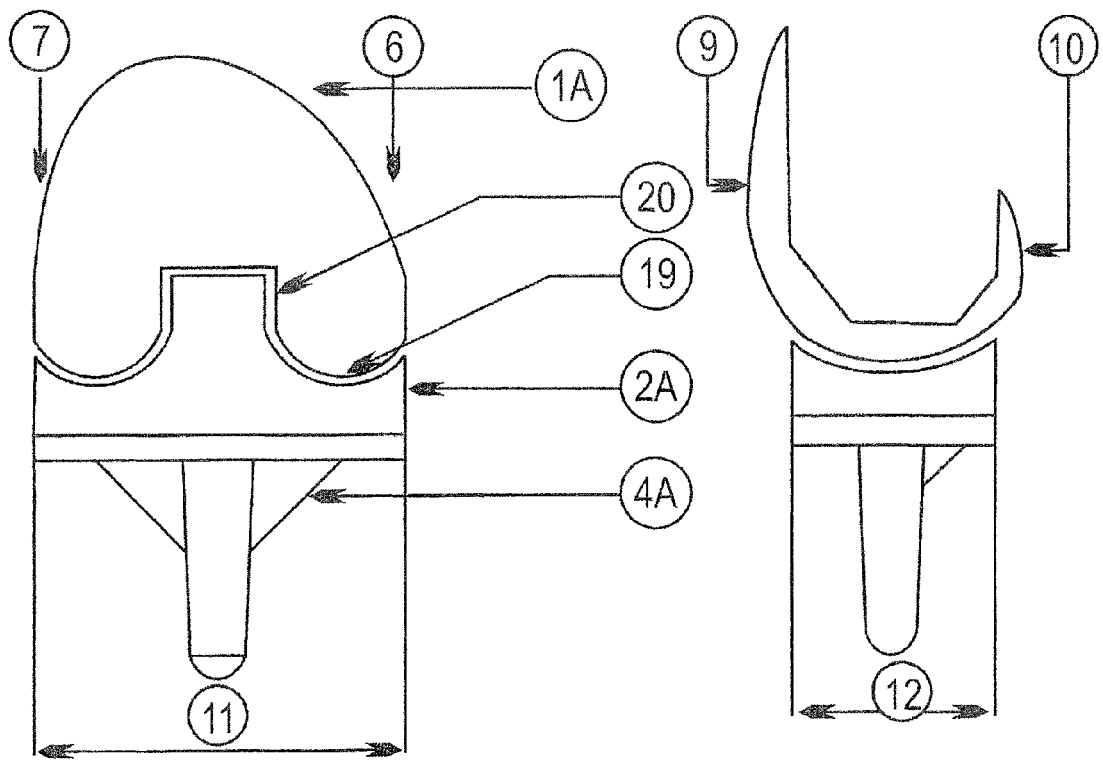
Fig : 3A         Fig : 3B
PERFECTLY CONFORMING GEOMETRY
(19) ⟶ Conforming dimensions at Condylar area
(20) ⟶ Conforming dimensions at Post area

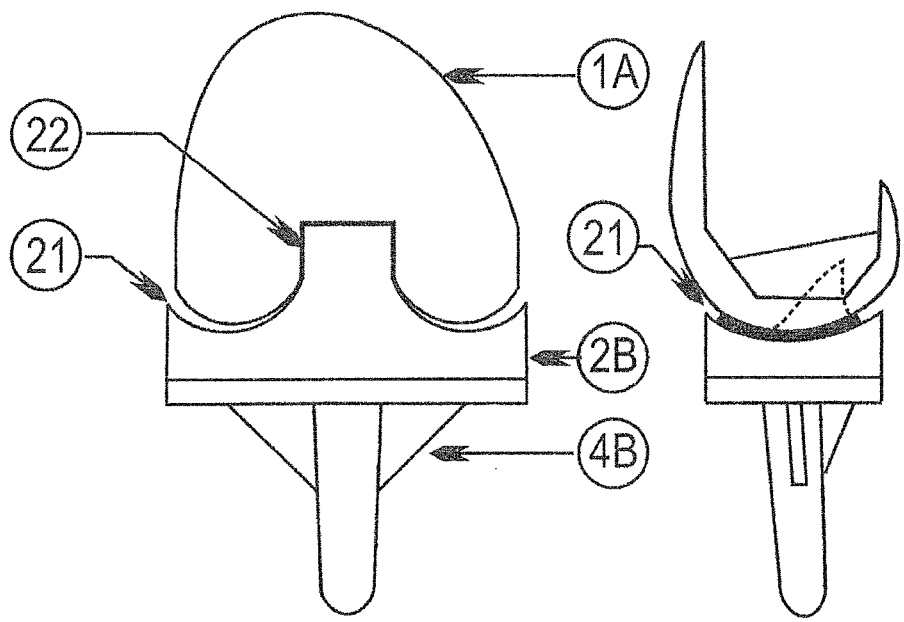
Fig : 4A  Fig : 4B
NON CONFORMING GEOMETRY. (CASE 1)
21 ➡ 'Loose fitting' dimensions at Condylar area
22 ➡ 'Tight fitting' dimensions at Post area

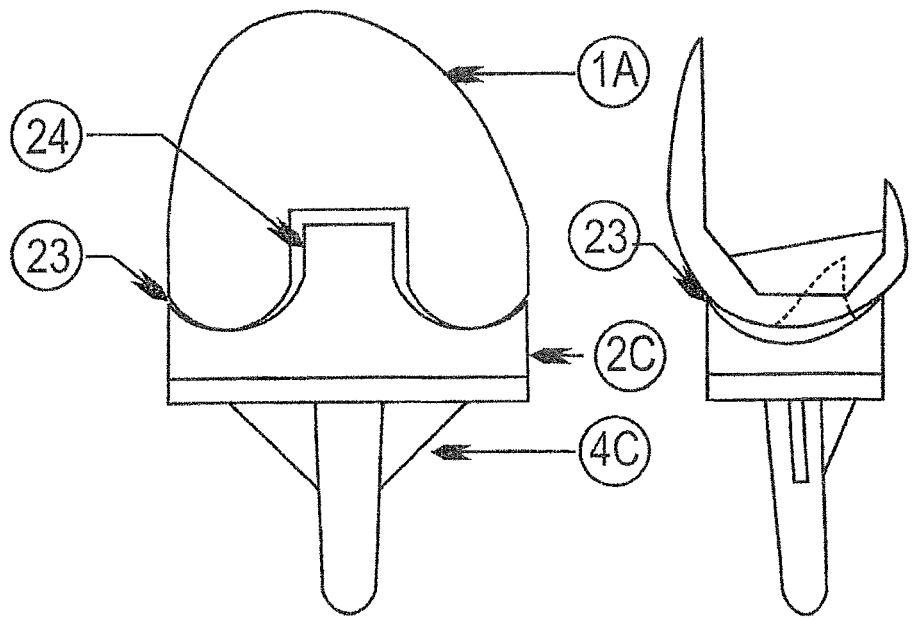
Fig : 5A      Fig : 5B
NON CONFORMING GEOMETRY. (CASE 2)
23 → 'Tight / Obstructing" dimensions of condylar area
24 → 'Loose fitting' dimensions at Post area

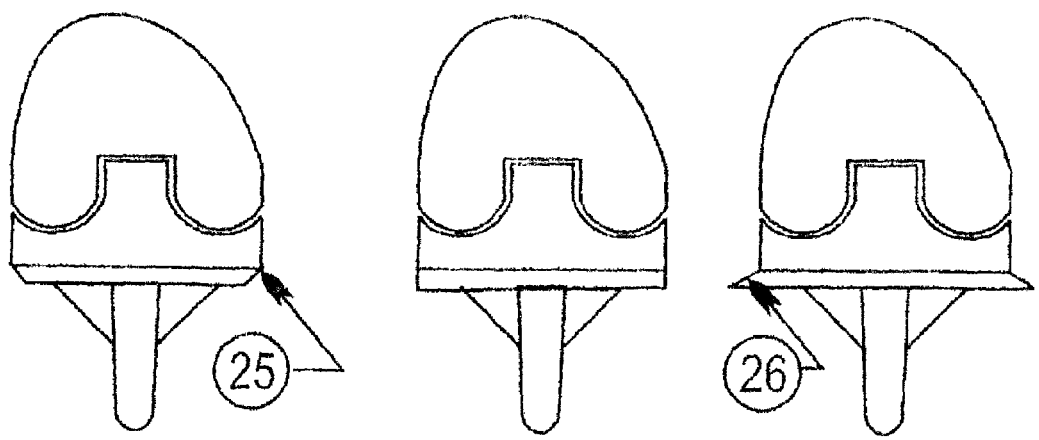
| TIBIAL COMPONENT MINUS DIMENSION | TIBIAL COMPONENT STANDARD DIMENSION | TIBIAL COMPONENT PLUS DIMENSION |
|---|---|---|
| FIG. 6A | FIG. 6B | FIG. 6C |

IMPLANT SET HAVING MODULARITY WITH CONFORMITY FOR TOTAL KNEE REPLACEMENT

CROSS REFERENCE TO RELATED APPLICATIONS

This application is a continuation of PCT/IN2014/000370 filed on Jun. 2, 2014, which claims priority from Indian application No. IN 623/MUM/2013 filed on Jun. 1, 2013, the entire contents of which are incorporated by reference.

BACKGROUND OF THE INVENTION

1. Field of the Invention

The invention relates to an implant set having modularity with conformity total knee replacement. More particularly this invention is meant to provide the exact conformity of femoral component (1) and tibial insert (2) and apt combination of femoral component (1) and tibial component (4).

2. Description of the Related Art

A) The total knee replacement Implant set consists of four components, namely, a femoral metal component, a tibial component (4), a tibial Insert (2) and a patella.

B) In some implant sets the tibial component (4) and tibial insert (2) are assembled together by manufacturer as one unit in which the tibial component (4) is made of metal and the insert is made of polyethylene.

C) In some implant sets this tibial component (4) tibial Insert (2) assembly is omitted and is replaced by an all poly tibial component (4) which has same dimension as that of tibial component (4) (metal) and tibial insert (2) (Polyethylene) assembly.

Type 'B' is known as a monoblock system.

Type' is known as an All Poly system.

In each of the above mentioned types there are various sizes available to match with the anatomical sizes of the patient i.e. size goes on increasing in 'anterior posterior' dimension and medial-lateral dimension. The size means the size of each component, such as the femoral component (1), tibial component (4) and tibial insert (2).

Thus there would be about 5 to 8 sizes of femoral components (1) and 5 to 8 sizes of tibial components (4) and tibial inserts (2).

Generally, in the prior art it is expected that in the monoblock system femoral component (1) will have corresponding tibial component (4). For example, Femoral components (1) will increase in size from smaller to larger and would be named as size 1, 2, 3, 4, 5, etc. In the same way, tibial components (4) will be named as size 1, 2, 3, 4, 5, etc. Therefore, size 1 of femoral components (1) will match with size 1 of tibial components (4) and so on.

But in day-to-day practice this logic is not suitable. The anatomy of the patient is different because of a number of parameters and conditions. Therefore, Femoral components (1) size 1 will not always match with tibial component (4) of size 1 in A/P and M/L dimensions.

It happens that size 2 of femoral components (1) will require size 1 tibial components (4) or size 3 tibial components (4A). This situation demands a 'modular system' of implants which will consist of femoral component (1), tibial component (4) and tibial insert (2) i.e. Type 'A' like system.

Currently, nearly all the implant sets are available are 'modular systems'.

This modularity allows the mix-n-match of the components in allowable limits prescribed by the designer/manufacturer. But this mix-n-match of the components in allowable limits always forces the user to make the compromise in the 'Conformity' of the 'Femoral component' (1) to tibial Insert (2)/tibial Component (4) assembly.

'Conformity' means the dimensional matching of the two articulating geometries i.e. in the current scenario geometrical matching of the articulating surface of femoral components (1) and tibial Insert (2).

It is always preferable to have the 'exact foot-print' of femoral component (1) on the tibial insert (2).

In case of 'mix-n-match' of the components the compromises are as follows:

The case 1: Referring to FIGS. 4A and 4B, indicate non-conforming dimension on tibial insert (2) and obstructing dimension of femoral component (1);

1) FIGS. 3A and 3B—Exactly conforming;
2) FIGS. 4A and 4B—Non conforming dimensions, e.g. tibial insert (2)/tibial component bigger than femoral component (1);
3) FIGS. 5A and 5B—Femoral component (1) bigger than tibial insert (2)/tibial component (4) assembly;

The case 2: Referring FIGS. 5A and 5B indicate non-conforming geometries of tibial insert (2) loose fitting dimensions on femoral component (1).

Thus, FIGS. 3A and 3B show the perfectly conforming geometry

FIGS. 4A and 4B show the 'loose' condylar and obstructing' notch dimensional fit.

FIGS. 5A and 5B show the 'loose' notch and obstructing condylar dimensional fit.

To avoid obstructing post (3) with box, the dimension of the "femoral box' (13) is increased for smaller size, i.e. femoral component (1) of size 1 will have the same box width as that of size 2.

To reduce the dimensional interference $wf > wp$ & $df > dp$, $wf > wp$ should go on increasing as size increases in relation to each other, $df > dp$ should go on increasing as size increases in relation to each other.

But because of current available modularity between implants, 1. to accommodate the post (3) of 'size 2 tibial insert' (2) in the box of 'size 1 femur' the box of size 1 femur must be widened and deepened, resulting in extra resection of bone (4A and 4B); case 1.

2. As in case 2, i.e. FIGS. 5A and 5B, where tibial insert (2) is of smaller size than femoral component (1), there will be excess clearance between femoral box (13) and tibial post (3), resulting in increased stress of the post (3) leading to faster wear of the post (3).

To avoid all these compromises described in case 1 or case 2, the solution is an implant set having modularity with conformity for total knee replacement according to the present invention.

SUMMARY OF THE INVENTION

It is the object of the present invention to develop an implant set having modularity with conformity for total knee replacement It is also the object of the present invention to have Total Knee Prosthesis systems which will be modular in nature and also will ensure proper conformity, stability, stress values and bone conservation.

It is another objective of the invention to provide a Total Knee Replacement Prostheses, wherein a basic principle is to offer modularity without sacrificing conformity, stability and extra bone removal.

Yet another object of the present invention is to eliminate the drawbacks and disadvantages of the prior art.

According to the disclosed embodiments, an implant set is provided having modularity with conformity for total knee replacement comprising femoral metal component, tibial component with locked tibial insert therein and Patella to provide the exact conformity of combination of femoral component and tibial component with number of sizes; the improvement involves in such a way that each of the size of the said Femoral component to tibial insert pair, there will be three sizes of tibial components available minus size tibial component, standard tibial component, plus size tibial component with the dimensions of the locking mechanism uniform on all the said three sizes i.e. on minus, standard and plus size tibia.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings:

Invention is described with reference to figures of drawing wherein:

FIGS. IA and 1B shows front and side view of total knee replacement Implant set. Illustrating medial-lateral (M/L) dimension (11) and anterior-posterior (A/P) dimensions (12) respectively;

FIGS. 2A and 2B shows front and side view of the femoral component (1) accommodating tibial insert (2) and from view shows width and depth of on femoral box (13) and width and depth of post (16).

FIGS. 3A and 3B shows front and side view of total knee replacement implant set illustrating articulating surfaces of femoral component (1) and tibial component (4);

FIGS. 4A and 4B shows front and side view of total knee replacement implant set illustrating non confirming dimension and obstructing dimension between femoral and tibial components (4);

FIGS. 5A and 5B shows front and side view of total knee replacement implant set illustrating non-conforming, loose fitting and obstructing dimensions;

FIGS. 6A, 6B and 6C show front view of total knee replacement implant set according to the present invention having confirming femoral and tibal insert geometry with variation in size plus or minus from standard size.

Reference number components list.

| NO. | Description | Ref. FIG No. |
|---|---|---|
| 1 | FEMORAL COMPONENT | 1A, 1B |
| 2 | TIBIAL INSERT | 1A.1B |
| 3 | POST | 1A.1B |

-continued

Reference number components list.

| NO. | Description | Ref. FIG No. |
|---|---|---|
| 4 | TIBIAL COMPONENT | 1A.1B |
| 5 | STEM OF TIBIAL COMPONENT | 1A.1B |
| 6 | MEDIAL SIDE | 1A.1B |
| 7 | LATERAL SIDE | 1A.1B |
| 8 | CONDYLAR AREA | 1A.1B |
| 9 | ANTERIOR SIDE | 1A.1B |
| 10 | POSTERIOR SIDE | 1A.1B |
| 11 | M/L (MEDIAL TO LATERAL) DIMENSION | 2A.1B |
| 12 | NP(ANTERIOR TO POSTERIOR) DIMENSION | 1A.1B |
| 13 | FEMORAL BOX | 2A.2B |
| 14 | ARTICULATING AREA | 2A.2B |
| 15 | W (WIDTH OF FEMORAL BOX) | 2A.2B |
| 16 | dp (DEPTH OF POST) | 2A.2B |
| 17 | dF (DEPTH OF FEMORAL BOX) | 2A.2B |
| 18 | Wp (WIDTH OF POST) | 2A.2B |
| 19 | CONFIRM DIMENSIONS IN CONDYLAR AREA | 3A.3B |
| 20 | CONFIRM DIMENSIONS IN POST AREA | 3A.3B |
| 21 | LOOSE FITTING DIMENSIONS IN CONDYLAR AREA | 4A.4B |
| 22 | TIGHT/OBSTRUCTING DIMENSIONS IN POST AREA | 4A.4B |
| 23 | TIGHT/OBSTRUCTING DIMENSIONS IN CONDYLAR AREA | 5A.5B |
| 24 | LOOSTE FITTING DIMENSIONS IN POST AREA | 5A.5B |
| 25 | MINUS SIZE PERIPHERAL SLOPE | 6A |
| 26 | PUUS SIZE PERIPHERAL SLOPE | 6C |
| 1A | FEMORAL COMPONENT SIZE | 3A.3B |
| 2A | TIBIAL INSERT SIZE 3 | 3A.3B |
| 4A | TIBIAL COMPONENT SZ.3 | 3A.3B |
| 2B | TIBIAL INSERT SIZE 4 | 4A.4B |
| 4B | TIBIAL COMPONENT SZ.4 | 4A.4B |
| 2C | TIBIAL INSERT SIZE 2 | 5A.5B |
| 4C | TIBIAL COMPONENT SZ 2 | 5A.5B |

DETAILED DESCRIPTION OF THE PRESENTLY PREFERRED EMBODIMENTS

Referring to FIGS. 6A, 6B, and 6C, the modularity according to the present invention is achieved without sacrificing conformity between curvatures of Insert and Femoral components (1) as well as relation between widths of post (3) of Insert and Box of Femoral component (1). For this present invention features in the Tibial component (4) for every size femoral component (1) and insert are matching of same size but present invention provides three options-minus, standard, plus, for every size of tibial components (4). According to the present invention geometry of peripheral areas of tibial trays, outer wall of tibial tray is straight for each nominal size as shown in FIG. 6B.

As shown in FIG. 6A, the outer wall of tibial tray is tapering inward (25) for each size with Minus variant, i.e. at proximal end the area of the tray will be same that of standard size but will reduce at distal end by tapering inwards to match with the standard area of tibial tray of one size minus.

As shown in FIG. 6C the outer wall of tibial tray is tapering outward (26) for each size with Plus variant, i.e. at proximal end the area of the tray will be same that of standard size but will increase at distal end by tapering outwards to match with the standard area of tibial tray of one size plus.

The inward and outward tapers (slopes) (25, 26) may be straight or curved as per the design requirement. Currently as shown in FIGS. 6A, 6B, 6C, stems of tibial component (5) of all three variants will remain same within each size.

According to this invention, Minus variant within each size will have stem of the tibial component (5) geometry same as standard variant of a smaller size and Plus variant within each size will have stem geometry same as stem geometry of standard variant of one size larger.

(Stem=distal (lower) part of tibial component (4), below the tray)

According to this invention, the exact conformity of femoral component (1) and tibial insert (2) and apt combination of femoral component (1) & tibial component (4) is achieved.

(Note:—In modular systems the tibial insert (2) is 'locked' on the tibial component (4) by a locking mechanisms which has various designs)

1) There will be 5 to 8 sizes of femoral components (1) and each size of femoral component (1) will have matching/conforming tibial insert (2).

2) For each Femoral component (1) to tibial insert (2) pair, there will be three sizes of tibial components (4) available viz. minus size tibial component (4), standard tibial component (4), plus size tibial component (4).

3) The dimensions of the locking mechanism will be same on all the three sizes, i.e. on minus, standard and plus size tibia.

For achieving such modularity current product sacrifice correctness of both fit and form between femoral and tibial components (4). For each size of tibial and femoral components (1) there is match of articulating geometries. Such match offers set of stresses and conformity. But in order to accommodate/match higher and lower sizes with each other these optimal match need to be altered resulting in higher stresses and worse conformity. Similar is the case with match of tibial post (3) and femoral groove. Typically these widths should go on increasing with increasing size. But to accommodate larger sized tibial post (3) each femoral notch need to be wider and/or width of the post (3) need to be narrower than otherwise necessary. This results in lesser stability between tibial post (3) and femoral component (1). Also it leads to cutting off larger than necessary portion of bone. The tibial components (4), according to invention, are specially designed. For each size we have more than one variant of tibial components (4). For each size, all variants have same post (3) width and also same articulating geometry. This ensures proper conformity and stability, good stress values and is better bone conserving. Having proper width for the post (3) also ensures proper articulation of femoral cam on Post (3). The followings are the sizes of tibial components (4) according to the design of the present invention

| Components | size | | | Size | | | size | | | Size | | | size | | |
|---|---|---|---|---|---|---|---|---|---|---|---|---|---|---|---|
| Femoral comp. (1) | 1 | | | 2 | | | 3 | | | 4 | | | 5 | | |
| Tibal insert (2) | 1 | | | 2 | | | 3 | | | 4 | | | 5 | | |
| Tibal component | −1 | 1 | +1 | −2 | 2 | +2 | −3 | 3 | +3 | −4 | 4 | +4 | −5 | 5 | +5 |

4) The minus size tibial tray will have peripheral chamfer on the undersurface edge i.e. the surface which will come in contact with the resected tibial bone as shown in FIG. 6 A.

5) The plus size tibial tray will peripheral chamfer on the peripheral edge of the surface on which tibial insert (2) is fitted as illustrated in FIG. 6 C Bones sizes are as per natural anatomy of each person. This would lead to a situation where tibial bone suites with one size of prosthesis while femoral bone suites with some other size. To address this need prostheses are designed such that each of tibial prostheses can be matched with plus or minus one or two sizes of femoral prosthesis. This is called modularity. To enable this modularity number of compromises needed to be done in prostheses design. We have sought to eliminate these deficiencies in our design.

Current products address this issue of size mismatch by sacrificing design parameters so that any size of tibial prostheses can be matched with a size or two plus or minus of size of femoral prosthesis. This is called modularity. Convex geometry of femoral component (1) articulate on concave geometry of tibial insert (2). These geometries are so designed for each so as minimize stress and wear and to give stability to joint. To achieve the above mentioned modularity these size specific optimal geometries are sacrificed and common geometries are designed for different sizes. This is adverse effect on stress and/or stability. In case of posterior stabilized prostheses designs there is protruding post (3) in tibial component (4) with corresponding notch in femoral component (1). Cam on femoral component (1) articulates on this tibial post (3). Widths and sizes of these notch and post (3) are size matching. But to achieve modularity of fitting a tibial post (3) into a different sized femoral notch, the notch widths need to wider and/or post (3) width narrower.

Thus an objective of this invention is achieved having a total Knee Prosthesis system which will be modular in nature and also will ensure proper conformity, stability, stress values and bone conservation.

This is Total Knee Replacement Prostheses design. Basic principle of the invention is to offer modularity without sacrificing conformity, stability and extra bone removal.

Metal femoral component (1) attached to distal femoral bone. Metal Tibial component (4) attached to tibial bone. Plastic Insert locked into metal tibial component (4). Insert has articulating geometry with femoral component (1) and has post (3). For above description plastic Insert and metal tibial component (4) together are called as one tibial component (4).

Femoral component (1) has a polished convex surface which articulates on plastic tibial Insert (2) to simulate natural knee movement. Size and shape wise all these components are attempted to match as closely as possible with natural anatomy of the patient and at the same time offer most optimal functionality.

ADVANTAGES OF THE PRESENT INVENTION

Advantages of the present invention over the prior art are believed to be:

1) Total Knee Prosthesis systems according to the present invention is modular in nature and also will ensure proper conformity, stability, stress values and bone conservation.

2) Total Knee Prosthesis systems according to the present invention offers modularity without sacrificing conformity, stability and extra bone removal.

3) Total Knee Prosthesis systems according to the present invention is flexible and allows mix and match of the components.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed:

1. An implant set having modularity with conformity for total knee replacement, comprising: a femoral metal component, a tibial component, a tibial insert and a locking mechanism which locks the tibial insert in the tibial component, and a patella to provide an exact conformity size of a combination of the femoral component and the tibial component with a number of sizes, wherein for a given size of said femoral component to tibial insert there is at least one of at least three variant sizes of tibial components available for the implant set, said at least three variant sizes include a minus size tibial component, a standard size tibial component, and a plus size tibial component, and wherein dimensions of the locking mechanism are uniform on all the at least three tibial component variant sizes.

2. The implant set of claim 1, wherein said minus size tibial component has a peripheral chamfer such that, for each size having a decreasing variant, at a proximal end the area of the component will be the same as that of an area of the standard size component but will reduce at a distal end by tapering inwards to match a standard area of a tibial component one size smaller, said plus size tibial component having a peripheral chamfer on its peripheral edge by tapering the outer wall of the tibial component outward for each size having an increasing variant at a proximal end, wherein the area of the component will be the same as that of the standard size but will increase at a distal end by tapering outwards to match an area of the tibial component one size larger.

3. The implant set of claim 2, wherein the set of five to eight sizes of femoral components is provided for selection and wherein each size of femoral component will have a corresponding tibial insert.

4. The implant set of claim 2, wherein said inward and outward tapers comprise a straight or curved configuration.

5. The implant set of claim 2, wherein each tibial component has a stem and wherein the size of the stem of all three variants remain the same as that of a standard variant.

6. The implant set of claim 2, wherein each tibial component has a stem and wherein the stem of the minus variant of the tibial component is smaller than the stem of the tibial component of the standard size.

7. The implant set of claim 2, wherein each tibial component has a stem, and wherein the stem of the plus variant of the tibial component is larger than the stem of the tibial component of the standard size.

8. The implant set of claim 1, further comprising a set of five to eight sizes of femoral components, wherein each size of femoral component has a corresponding tibial insert.

9. The implant set of claim 1, wherein said tibial component comprises inward and outward tapers of straight or curved configuration.

10. The implant set of claim 1, wherein the tibial component has a stem of a size and wherein all three variants remain the same as that of a standard variant.

11. The implant set of claim 1, wherein each of the tibial components has a stem, said stem of the minus variant being smaller than the stem of the tibial component of the standard size.

12. The implant set of claim 1, wherein each of the tibial components has a stem, said stem of the plus variant being larger than the stem of the tibial component of the standard size.

* * * * *